(12) United States Patent
Holladay et al.

(10) Patent No.: US 6,610,048 B1
(45) Date of Patent: Aug. 26, 2003

(54) PROLATE SHAPED CORNEAL RESHAPING

(76) Inventors: Jack T. Holladay, 5108 Braeburn Dr., Bellaire, TX (US) 77401; Travis D. Terry, 5824 Auvers Blvd., #105, Orlando, FL (US) 32807; Lance R. Marrou, 9313 Pine Meadows Ct, Orlando, FL (US) 32825; Michael J. Smith, 10143 Rivers Trail Dr., Orlando, FL (US) 32817

( * ) Notice: Subject to any disclaimer, the term of this patent is extended or adjusted under 35 U.S.C. 154(b) by 232 days.

(21) Appl. No.: 09/679,077

(22) Filed: Oct. 5, 2000

Related U.S. Application Data (60) Provisional application No. 60/223,728, filed on Aug. 8, 2000, and provisional application No. 60/157,803, filed on Oct. 5, 1999.

(51) Int. Cl.⁷ .............................................. A61B 18/18
(52) U.S. Cl. ........................................................ 606/5
(58) Field of Search ........................... 606/5, 6, 4, 107, 606/166

(56) References Cited

U.S. PATENT DOCUMENTS

| | | |
|---|---|---|
| 4,050,192 A | 9/1977 | Volk |
| 4,420,228 A | 12/1983 | Humphrey |
| 4,660,946 A | 4/1987 | Nakamura et al. |
| 4,710,193 A | 12/1987 | Volk |
| 4,732,148 A | 3/1988 | L'Esperance |
| 5,110,200 A | 5/1992 | Snook |
| 5,325,134 A | 6/1994 | Kohayakawa |
| 5,350,374 A | 9/1994 | Smith |
| 5,411,501 A | 5/1995 | Klopotek |
| 5,549,597 A | 8/1996 | Shimmick et al. |
| 5,640,962 A | 6/1997 | Jean et al. |
| 5,644,396 A | 7/1997 | Hopkins, II |
| 5,695,509 A | 12/1997 | El Hage |
| 5,735,283 A | 4/1998 | Snook |
| 5,841,511 A | 11/1998 | D'Souza et al. |
| 5,861,955 A * | 1/1999 | Gordon ...................... 356/511 |
| 5,886,767 A | 3/1999 | Snook |
| 5,997,529 A | 12/1999 | Tang et al. |
| 6,033,396 A | 3/2000 | Huang et al. |
| 6,045,578 A | 4/2000 | Collins et al. |
| 6,080,144 A | 6/2000 | O'Donnell, Jr. |
| 6,082,856 A | 7/2000 | Dunn et al. |
| 6,129,722 A * | 10/2000 | Ruiz ............................. 606/5 |
| 6,302,977 B1 * | 10/2001 | Liu ............................ 148/671 |
| 6,322,555 B1 * | 11/2001 | LaHaye ........................ 606/5 |
| 6,409,718 B1 * | 6/2002 | Tang ............................. 606/5 |

FOREIGN PATENT DOCUMENTS

| | | |
|---|---|---|
| EP | 0 628 298 A1 | 12/1994 |
| WO | WO 9527452 | 10/1995 |

OTHER PUBLICATIONS

Achim Langenbucher et al., Ellipsoidal Fitting of Corneal Topography Data After Arcuate Keratomies with Compression Sutures, Ophthalmic Surgery and Lasers, Sep. 1998, pp. 738–748.

* cited by examiner

Primary Examiner—Daniel Robinson (57) ABSTRACT

Apparatus and techniques for performing prolate shaped corneal reshaping. In accordance with the techniques, an ablation scanning laser system includes fitter modules to fit input refractive or topographical measurement data to a three (3) variable ellipsoid model. This provides pre- and post-operative approximations of a cornea. A desired prolate shaped ablation profile is determined based on a desired prolate ellipsoidal shape. In accordance with the principles of the present invention, the spheroequivalent ellipsoid model has only three degrees of freedom (not four as in a conventional biconic technique) to define a desired ablation profile, providing extremely accurate and predictable long term vision correction. To arrive at an ellipsoid model having only three numbers of freedom, a spheroequivalent (SEQ) value of asphericity $Q_{SEQ}$ is generated. The spheroequivalent eccentricity $Q_{SEQ}$ value replaces two degrees of freedom (i.e., eccentricities) in an otherwise conventional biconic modeling system, leaving only three (3) variables to determine for a best fit ellipsoid to a corneal surface, to make accurate prolate ellipsoidal modeling of a cornea possible, and to limit results to regular astigmatism that can be corrected with optical spherocylinders.

8 Claims, 5 Drawing Sheets

PROLATE SHAPED CORNEAL RESHAPING

The present invention claims priority from U.S. Provisional Application No. 60/157,803 filed Oct. 5, 1999, entitled "Method and Apparatus for Using an Ellipsoidal Surface Shape for Corneal Reshaping" to Jack Holladay; and U.S. Provisional Application No. 60/223,728 filed Aug. 8, 2000 entitled "Custom Prolate Shape Corneal Reshaping" to Jack Holladay, the entirety of which are each expressly incorporated herein by reference.

BACKGROUND OF THE INVENTION

1. Field of the Invention

This invention relates generally to apparatus for use in reshaping the cornea of a human eye. More particularly, it relates to human corneal refractive surgery and techniques and apparatus used to model the human eye as an ellipsoid to determine a desired refractive correction.

2. Background of Related Art

First generation ablating excimer laser systems are characterized by relatively large diameter laser beams (6 mm), low laser pulse repetition rates (10 Hz), and mechanical means for shaping the resultant ablation profile. These older generation systems cannot achieve the accuracy required to shape the ablation profiles described in this disclosure, nor do they have the resolution necessary to achieve optimal refractive results. The excimer laser system described herein is a later generation system incorporating a small diameter laser beam (1 mm), operating at relatively high laser pulse repetition rate (100–200 Hz), and incorporating computer controlled x-y scanning to control the ablation pattern.

Figure 4A:
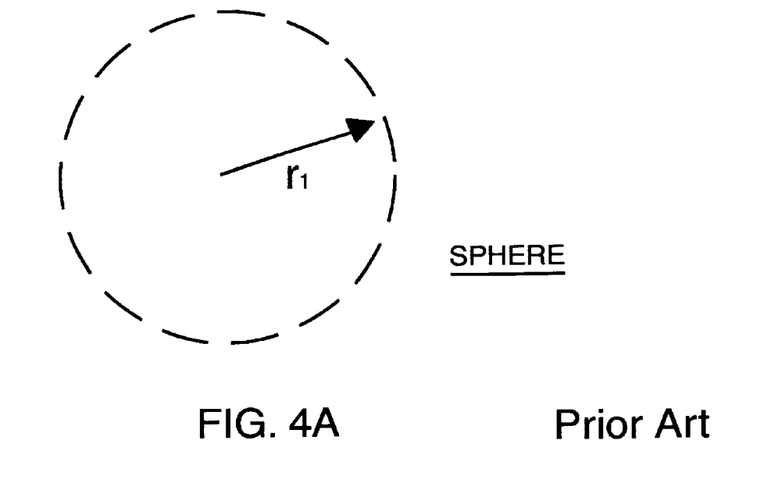
FIG. 4A shows a conventional technique for performing refractive surgery which assumes that the human eye is a spherical globe of a certain radius of curvature $r_1$.

A model of the human eye is used for the initial and target shapes for corneal refractive surgery. The currently utilized technique for planning refractive surgery assumes that the human eye is a spherical globe of a certain radius of curvature $r_1$, as depicted in FIG. 4A. To correct refractive errors, a spherical globe of lesser or greater curvature is targeted to achieve the ideal patient refraction. The intersection between these two globes provides the amount of material to remove from the patient's cornea in order to achieve the target refraction.

Figure 4B:
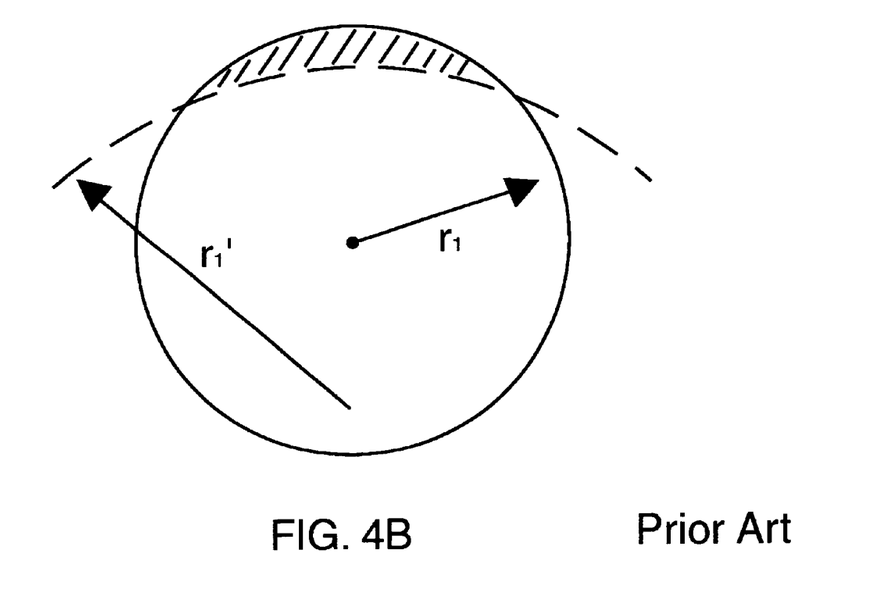
FIG. 4B depicts a Munnerlyn model of a cornea wherein a presumed spherical cornea is ablated to a desired spherical shape having a single radius $r_1'$.

FIG. 4B depicts a Munnerlyn model wherein a presumed spherical cornea is ablated to a desired spherical shape having a single radius $r_1'$. Using this model, the target corneal surface is always a spherical shape.

However, the cornea is not exactly spherical, and ablation systems and techniques which determined a closest fit sphere to a patient's cornea where somewhat inaccurate because of the differences between the actual shape of the cornea and the best fit sphere modeling the cornea used by the ablation system.

Corneal ablation surgery was then extended to use initial and target toroidal surfaces instead of spheres to allow for correction of astigmatic refractive error. Astigmatisms are refractive errors that occur along two different radii.

Figure 5A:
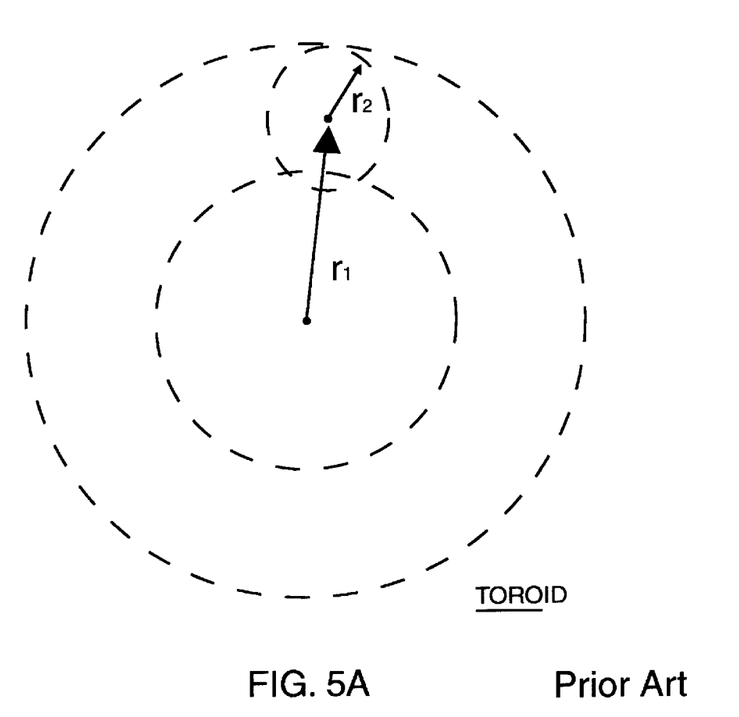
FIG. 5A shows an advanced model of a cornea as a toroidal surface including a major radius $r_1$ and a minor radius $r_2$.

A toroidal surface might be thought of as an 'inner tube' shape, with a major radius $r_1$ (the radius of the whole tube) and a minor radius $r_2$ (the radius of a cross sectional area of the tube), as shown in FIG. 5A. Thus, the art had moved from models having a single radius (i.e., spheres) to models having two radii (i.e., toroids).

Figure 5B:
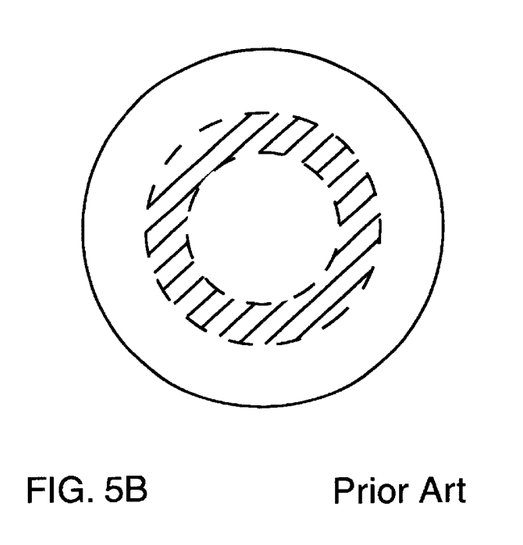
FIG. 5B shows an exemplary toroidal ablation pattern is shown from above the cornea in FIG. 5B.

The toroidal surface, however, makes the assumption that the eye shape is circular along any meridian through the optical center of the eye's surface. An exemplary toroidal ablation pattern is shown from above the cornea in FIG. 5B. However, in practice, this is rarely the case, and toroidal surfaces too cause inaccuracies in ablation systems due to the differences between the best fit toroidal surface and the actual shape of the patient'.

The human eye is perhaps best modeled by using an ellipsoid instead of a toroid or a sphere. If an ellipsoid is used to model the human eye, the prolate shapes, or surfaces, of the ellipsoid can be used to more accurately describe the true shape of the eye. A prolate shape is one having its polar axis longer than its equatorial diameter. Substituting the ellipsoid shape instead of the toroid shape can then be used to determine the corneal tissue to remove.

The ellipsoid shape is a surface in which all plane sections perpendicular to any axis of which are ellipses or circles. The normally flatter portions of the ellipsoid shape are considered as oblate or flattened or depressed at the poles. The steeper areas of the ellipsoid are considered as prolate or elongated in the direction of a line joining the poles. The currently applied models of the human eye utilized to plan ablation profiles assume corneal surfaces that approximate an oblate shape. Light rays refracted through the oblate surface are not confocal; i.e. they do not have the same foci.

The result of this inability to achieve a confocal condition frequently results in glare, halos, and loss of night vision.

While the advantages of ellipsoidal modeling of a cornea have been noted, conventional corneal modeling uses a biconic technique which requires the solution of four (4) or more parameters (e.g., two radius values, two eccentricity values). The use of the ellipsoid equation on eccentricity has not been used, only the biconic.

There is thus a need for an ablation laser system and method which utilizes accurate ellipsoidal modeling for precise and realistic refractive correction of corneas.

SUMMARY OF THE INVENTION

In accordance with one aspect of the present invention, a prolate corneal modeler in a corneal laser ablation system comprises a corneal measurement input module, and an ellipsoid fitter. The ellipsoid fitter generates a best ellipsoid fit to corneal data input to the ellipsoid fitter using an ellipsoid algorithm having only three degrees of freedom.

A method of modeling a corneal surface in accordance with another aspect of the present invention comprises receiving corneal measurement data, and fitting the corneal measurement data to a best fit ellipsoid having only three degrees of freedom.

A method of ablating a cornea into a prolate shape in accordance with still another aspect of the present invention comprises determining a desired ablation pattern to form a prolate shaped ellipsoid on a surface of the cornea. An eccentricity of the prolate shaped ellipsoid is adjusted to intentionally leave approximately 10% astigmatism on an ablated surface of the cornea to cancel an astigmatic condition on a posterior side of the cornea and any contribution from lenticular astigmatism. The cornea is ablated in accordance with the adjusted prolate shaped ellipsoid.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

The present invention provides apparatus and techniques for performing prolate shaped corneal reshaping. In accordance with the techniques, a spheroequivalent ellipsoid model is implemented to provide a pre- and post-operative approximation of a cornea, and a desired prolate shaped ablation profile is determined based on a desired ellipsoidal shape. In accordance with the principles of the present invention, the ellipsoid model has only three degrees of freedom (not four as in a conventional biconic or toric techniques) to define a desired ablation profile, providing extremely accurate and predictable long term vision correction.

To arrive at an ellipsoid model having only three numbers of freedom, a spheroequivalent (SEQ) value of eccentricity $\epsilon$ or asphericity Q $(1+Q_{SEQ})=(1-\epsilon_{SEQ}^2)$ is generated. The eccentricity $\epsilon$ value replaces two numbers of freedom (i.e., eccentricities) in an otherwise conventional biconic modeling system, leaving only three (3) variables to determine for a best fit ellipsoid to a corneal surface, to make accurate prolate ellipsoidal modeling of a cornea possible.

The disclosed embodiment of the present invention is specifically related, but not limited, to corneal refractive surgery performed with an ablating laser. An example of an ablating laser system is the LaserScan™ LSX excimer laser system available from LaserSight Technologies, Inc., Winter Park, Fla. While the description of the invention is related to laser corneal ablation, the method described herein is equally applicable to other laser systems such as tempto second laser, holmium, etc., and other techniques for corneal correction that include ALK, PTK, RK, and others.

The method and apparatus disclosed herein utilizes a model that plans the ablation profile based on generating a prolate shape on the corneal surface, and an excimer laser apparatus with a computer controlled scanning system to ablate the desired profile onto the corneal surface. The prolate surface refracts rays into a better focus configuration, thereby minimizing the occurrence and effects of glare, halos, and loss of night vision from aberrations inherent in an oblate shape.

In conventional corneal ablation procedures, only one surface of the cornea is ablated or corrected. For instance, while the anterior corneal surface is ablated, the posterior surface remains as it was before the corrective surgery. However, the present inventors realized that when correcting for astigmatism on a corneal surface, some amount of astigmatism should essentially be left on the front surface to correct for correlating astigmatism existing on an opposite surface of the cornea and the crystalline lens.

Ellipsoidal surface modeling allows an ablation system to actually leave some astigmatism on the ablated corneal surface, e.g., on the anterior corneal surface, to neutralize astigmatism on the opposite side of the cornea, e.g., on the posterior surface and from the crystalline lens.

In particular, in the case of astigmatism, it is determined that an amount of residual astigmatism (e.g., 10% of the astigmatism) is preferably left on the ablated front corneal surface to neutralize the related astigmatic error on the back corneal surface. This is particularly why spherical modeling and spherical shaped ablation patterns will not totally correct astigmatism: because it cannot correct for the astigmatic condition also existing on the posterior surface of the cornea. For instance, if a particular cornea is measured to have 10 diopters of net astigmatism (+11 diopters on the front of the cornea, and −1 diopter on the posterior surface). In such a case, a 10 diopter correction is preferred to leave +1 diopters on front surface to balance out a presumed −1 diopter astigmatism on the posterior surface of the cornea.

Biconics require an eccentricity parameter in each radial direction, thus there are conventionally at least four parameters of freedom which must be determined to define a particular pre- or post-operative corneal surface. Thus, to fit a biconic to a corneal surface, at least four variables must conventionally be 'solved'.

For instance, as pointed out in an article entitled "Ellipsoidal Fitting of Corneal Topography Data After Arcuate Keratotomies With Compression Sutures" by Achim Langenbucher, Berthold Seitz, Murat Kus, Ernesto Vilchis, and Michael Kuchle ("Langenbucher"), the problem is to fit a biconic to corneal dioptric power data. This article is expressly incorporated herein by reference.

Langenbucher implements a simplex algorithm to approximate a model biconic function defined by four (4) or more numbers of freedom to a corneal surface characterized by axial power data. The best fit is defined as a model surface minimizing the distance between the measured dioptric power data of the actual corneal surface and the dioptric power data of the model surface, e.g., using root mean square (RMS) error of the distance.

Generally speaking, the conventional four variables for which to solve, or the four numbers of freedom of the biconic function are the first radius $r_1$, the first eccentricity $\epsilon_1$, the second radius $r_2$, and the second eccentricity $\epsilon_2$. The eccentricities $\epsilon_1, \epsilon_2$ essentially define the amount of ovalness to the relevant surface. The greater the eccentricity, the greater the oval.

Langenbucher used all four degrees of freedom in a biconic, but didn't realize that both asphericities or eccentricities $Q_1, Q_2$ couldn't be specified using the ellipsoid to model the corneal surface data. The present invention appreciates that using a biconic ellipsoidal model with four (4) degrees of freedom, all four degrees can't be fully solved or ideally fit to otherwise conventional stereo topographical input data, only three (3) parameters can be used for the ellipsoid ($r_1, r_2, \epsilon$).

The present invention provides apparatus and techniques which provide an ellipsoidal model having only three (3) degrees of freedom. Using conventional refractive measurements (e.g., stereo topography measurements of the corneal surface), these three degrees or numbers of freedom can be accurately solved to fit conventional topographical input data to model the corneal surface.

In accordance with the principles of the present invention, the ellipsoidal model is reduced to only three (3) degrees of freedom, allowing a more accurate solution and more accurate post-operative results. Thus, a clinical target of a post operative ellipse is utilized in the biconic model to reduce the four (4) degrees of freedom in Langenbucher's system to only three (3). The biconic does not have elliptical cross-sections and does not truly reflect regular astigmatism.

In particular, the present invention utilizes apparatus and techniques which replace the two eccentricities $\epsilon_1, \epsilon_2$ of the conventional ellipsoidal model with a single spheroequivalent eccentricity $Q_{SEQ}$. In accordance with the principles of the present invention, the average eccentricity of a human cornea is $\epsilon=+0.51$, or in other words, $Q_{SEQ}=-0.26$.

Using the spheroequivalent eccentricity $Q_{SEQ}$, the present invention defines and provides a 'spheroequivalent' ellipsoidal model of a cornea, which essentially is an ellipsoidal equation solved for an average human', leaving only three (3) variables to be processed for a best fit to corneal measurement data.

The formula for defining an ellipsoid requires three parameters (along an x-axis defined as $r_x$, along a y-axis defined as $r_y$, and $\epsilon$ spheroequivalent eccentricity. These parameters can be directly applied to a grided area centered about the origin utilizing a pseudo-code. The $r_x$ and $r_y$ values are given directly as the curvature values normally used by the toroid derivation. In accordance with the principles of the present invention, the additional $\epsilon$ parameter may be defined by the eccentricity parameter $\epsilon_{SEQ}$.

The spheroequivalent eccentricity $\epsilon_{SEQ}$ is derived as follows:

The spheroequivalent ellipsoidal model requires a first keratometric value $K_1$ at a first axis (e.g., the x-axis), and a second keratometric value $K_2$ at a second axis (e.g., the y-axis).

Then, these constants $K_1$, $K_2$ are converted into two-dimensions including the z-axis. In particular, the first constant $K_1$ value is converted to another constant in two-dimensions $K_{XZ}$, and the second constant $K_2$ value is converted to another constant in two-dimensions $K_{YZ}$. This involves rotation with respect to the x-axis and the y-axis when they are not with-the-rule (90°) or against-the-rule (180°), which would be the case for a patient with oblique astigmatism.

In accordance with the principles of the present invention, given only the K values, the eccentricity is assumed. In the disclosed embodiments, post-operative corneal topography data is used to empirically determine a mean eccentricity value. The exemplary and preferred post-operative eccentricity value is $e_{SEQ}$=+0.51, or $Q_{SEQ}$=−0.26.

To convert to radii, we have from the keratometric formula, the following equations (1):

$$R_{XZ} = \frac{337.5}{K_{XZ}} \quad \text{and} \quad R_{YZ} = \frac{337.5}{K_{YZ}}$$

wherein $R_{XY}$ and $R_{YZ}$ are radius in millimeters, and the constants $K_{XZ}$ and $K_{YZ}$ are in diopters.

In accordance with the principles of the present invention, a spheroequivalent constant K value, $K_{SEQ}$, is defined as shown in the following equations (1b):

$$K_{SEQ} = \frac{K_{XZ} + K_{YZ}}{2}$$

The keratometric index of the keratometer used for measurement is factored in to arrive at an equation for the spheroequivalent radius $R_{SEQ}$. Note that the keratometric index is not standardized from one keratometer to another. In the disclosed embodiment, a keratometer manufactured by HUMPHREY™ was used, having a particular keratometric index of 337.5. Of course, the present invention relates to any keratometer having any keratometer index, e.g., 333.6, 333.2, etc.

The equation for the spheroequivalent radius $R_{SEQ}$ using the keratometer index of the HUMPHREY™ keratometer is:

$$R_{SEQ} = \frac{337.5}{K_{SEQ}}$$

Another equation for the spheroequivalent radius $R_{SEQ}$ is:

$$R_{SEQ} = \frac{2R_{XY}R_{YZ}}{R_{XY} + R_{YZ}}$$

Combining these last two equations for $R_{SEQ}$, we arrive at:

$$\frac{337.5}{K_{SEQ}} = \frac{2R_{XZ}R_{YZ}}{R_{XZ} + R_{YZ}}$$

Assuming the vertex of the cornea is the positive z-intercept, we have the radius values $R_{XZ}$, $R_{YZ}$ and an assumed average eccentricity $e_{SEQ}$ or asphericity $Q_{SEQ}$.

The general form of an ellipsoid is shown in the following equation (2):

$$\frac{x^2}{a^2} + \frac{y^2}{b^2} + \frac{z^2}{c^2} = 1$$

which equates to:

$$\frac{x^2}{R_{XZ}c} + \frac{y^2}{R_{YZ}c} + \frac{(z-z_{\max})^2}{c^2} = 1$$

where the constraining equation that provides the proprietary ellipsoidal model form derives from average radius of a cornea, in spheroequivalent power.

$$c = \frac{R_{SEQ}}{(1+Q_{SEQ})}$$

This leads to equation (3a):

$$\frac{x^2}{(R_{XZ}R_{SEQ})/(1+Q_{SEQ})} +$$

$$\frac{y^2}{(R_{YZ}R_{SEQ})/(1+Q_{SEQ})} + \frac{(z-z_{\max})^2}{\{R_{SEQ}/(1+Q_{SEQ})\}^2} = 1$$

Using the mean value eccentricity and asphericity for the human population ($Q_{SEQ}$=−0.26, $e_{SEQ}$=+0.51), we have equation (3b):

$$\frac{x^2}{(R_{XZ}R_{SEQ})/(0.74)} + \frac{y^2}{(R_{YZ}R_{SEQ})/(0.74)} + \frac{(z-z_{\max})^2}{\{R_{SEQ}/(0.74)\}^2} = 1$$

Solving for z, from equation (3a) we have:

$$z = z_{\max} \mp c^* \sqrt{\left(1 - \frac{x^2}{R_{XY}c} - \frac{y^2}{R_{YZ}c}\right)}$$

where values of x must be between $-R_{XZ}$ and $+R_{XZ}$, and values for y must be between $-R_{YZ}$ and $+R_{YZ}$.

This is the final equation for a spheroequivalent ellipsoidal model for a patient with known values of K, and an assumed mean population eccentricity (asphericity) to create an ellipsoid model having only three (3) variable parameters, in accordance with the principles of the present invention.

The resulting actual asphericity in the xz and yz planes is related to the spheroequivalent eccentricity $Q_{SEQ}$ by the following equations (5a) and (5b).

$$c = \frac{R_{XZ}}{(1+Q_{XZ})}$$

$$c = \frac{R_{XY}}{(1+Q_{XY})}$$

In practice, pre-operative refractive measurements and keratometry or topography measurements are taken for the patient's cornea to obtain per-operative front surface power measurements. Typically, the refractive measurements include refraction, K readings, and asphericity. Generally speaking, no two patients have the same refractive measurements.

In accordance with the principles of the present invention, these measurements are fitted into an ellipsoid having three numbers of freedom, $K_1$, $K_2$ and $Q_{SEQ}$. This defines an ellipsoid (prolate) shape. Essentially no patient has a perfect ellipsoidal shaped cornea, so a best fit three (3) parameter ellipsoid is determined, defined by $K_1$, $K_2$, and $Q_{SEQ}$.

A best fit ellipsoid having three (3) numbers of freedom is determined based on patient refractive measurement data, and a difference between an ideal ellipsoid and the best fit spheroequivalent ellipsoid is determined, forming the basis of the ablation profile.

The input measurement data may be smoothed prior to computing a best fit ellipsoid. For instance, a bivariate Fourier series smoothing program provides adequate smoothing of topographical input data in the disclosed embodiments to present more uniform input data to a best fit three (3) parameter ellipsoid module to arrive at a more accurate ellipsoidal model. An exemplary Fourier series bivariate may use either two variable $2^{nd}$ order to two variable $5^{th}$ order smoothing.

Alternatively, or additionally, the smoothing may be performed on the difference data between the pre-operative refractive measurement data and the ideal three (3) parameter spheroequivalent ellipsoid, to generate an irregular difference matrix from the best fit preoperative ellipse.

Additional or alternative smoothing may be performed, e.g., by visually reviewing three-dimensional graphical results to look for sports or outlying data points and/or high frequency components.

In the given embodiment, the final smoothed difference matrix determines a custom ablation component, i.e., the desired ablation profile.

Then, the ablation of the difference is performed. Post operation, the resulting corneal shape is measured topographically. The resulting corneal shape should ideally fit the ideal spheroequivalent ellipsoid as programmed into the ablation system. However, outside factors may and do influence the actual ablation profile (e.g., poor height data, interference from ablation plumes, moisture buildup on the cornea, etc.) In particular, the low resolution of height data is believed to be a major factor in delta measurements between the desired ideal ellipsoidal shape and the actual post-operative ellipsoidal shape of the cornea. For instance, height data from a commercially available ORBSCAN™ refractive measurement device is believed to have undesirable resolution of height data for the purposes of the present invention. However, a commercially available EYESYS™ topographical system is found to provide adequate corneal surface height data, particularly when augmented by integration between the 51×51 matrix of measurement points using curvature data to provide integrated height data between measurement points.

However, in accordance with the principles of the present invention, these differences are repeatable and predictable, and can generally be overcome with the inclusion of a calibration matrix corresponding to the ablation area to increase or decrease ablation in certain areas of the surface.

For instance, in one embodiment of the present invention, a delta $Q_{SEQ}$ correction factor matrix is established to compensate for differences between the ideal three (3) parameter ellipsoid and the shape of the post-operative cornea. The $Q_{SEQ}$ correction factor matrix preferably corresponds to each of the points of measurement of the measurement system (e.g., topographical input data matrix), and relates to a depth of ablation difference at each measurement point between what was expected of the scanning ablation system and what actually results from patient to patient, essentially 'correcting' each of the measurement points taken pre-operatively. Different depths of ablation have different delta $Q_{SEQ}$'s. In this way, an ablation profile will be established by the ablation system based on actual pre-operative data and adjusted per the $Q_{SEQ}$ correction factor matrix to result in the ideally shaped cornea post-operatively.

The $Q_{SEQ}$ correction factor matrix may be established empirically. Current embodiments utilize topographical height data and a 51×51 point correction matrix.

Empirical information can be used to refine the correction matrix. For instance, an 'average' compensation factor can be derived for each of the 51×51 points based on a difference between expected ablation depth (i.e., pre-operation value) and actual ablation depth (i.e., post-operation value), and a compensation factor can be used to correct the expected ablation depth to be equal to the presumed actual ablation depth. The compensation factors form a transfer function matrix.

For instance, in some refractive procedures it was seen that an ablation system induced slightly more oblateness from the ideal ellipsoid. Use of a correction factor matrix can refine the amount of induced oblateness to result more closely in the desired prolate ellipsoidal shape. The correction factor matrix may be refined empirically for particular laser ablation systems by adjusting initial K-values and/or Q-values in addition to the amount of treatment.

Prolate ablation using accurate three (3) parameter ellipsoid modeling provides important advantages, particularly over conventional spherical, toric and biconic techniques. For instance, if a person's pupil is between about 2.8 mm and 6 mm, it is found that spherical modeling is not preferred because the spherical aberration may be too great. If the pupil is greater than about 6 mm, using spherical modeling the cornea would no longer be prolate after surgery, degrading the optics of the eye and resulting in spherical aberration, resulting in halos and glare to the patient.

Prolate ablation using ellipsoidal modeling with three (3) degrees of freedom in accordance with the principles of the present invention is best used with regular astigmatism. As discussed, bi-conic modeling is disadvantageous because the four (4) degrees of freedom can produce a shape whose cross-section is not an ellipse and cannot be corrected to sphero-cylindric lenses (i.e., regular astigmatism).

Figure 1:
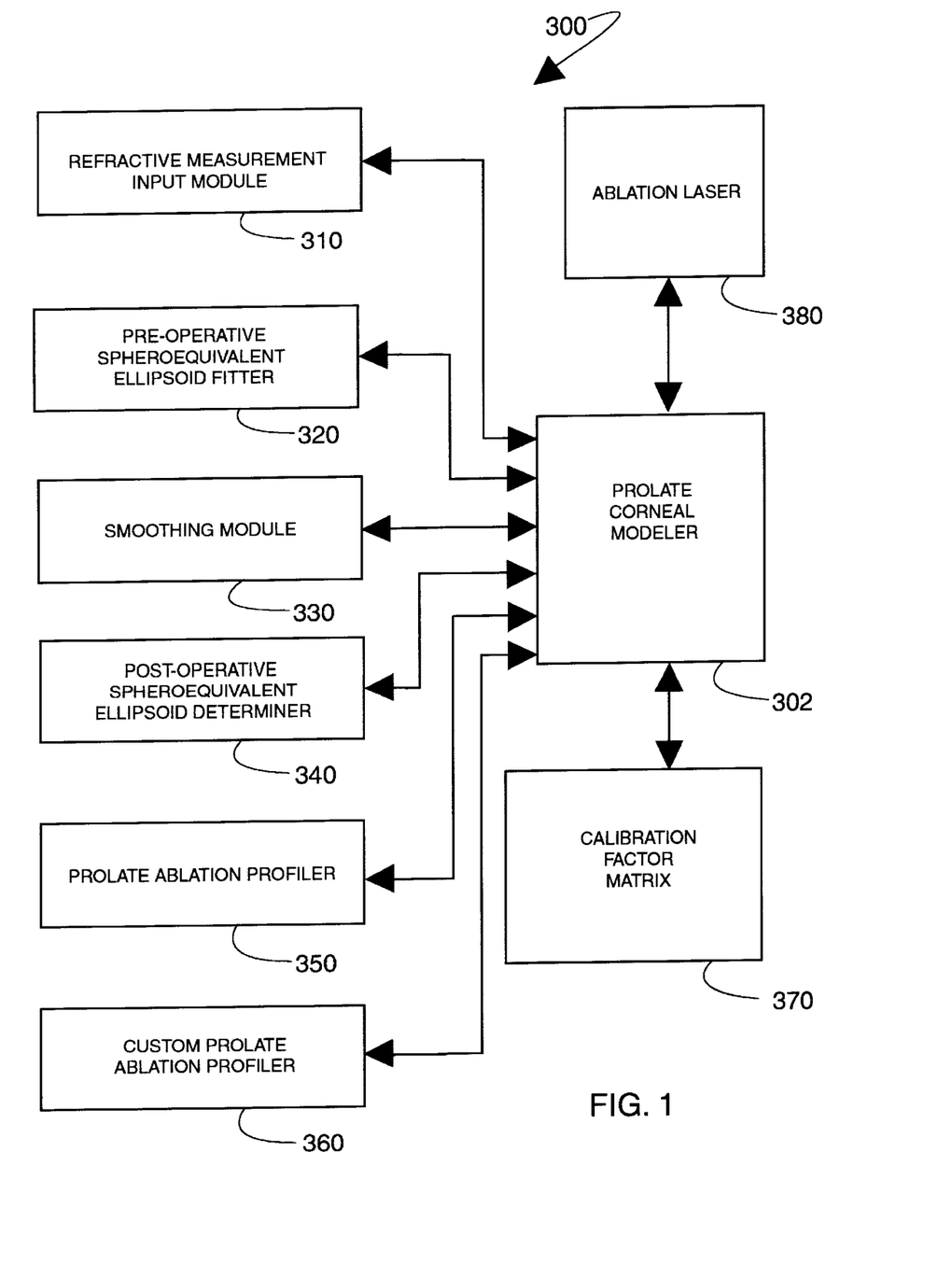
FIG. 1 shows an exemplary laser ablation system including ellipsoid modeling control, in accordance with the principles of the present invention.

FIG. 1 shows an exemplary laser ablation system including spheroequivalent ellipsoid modeling control, in accordance with the principles of the present invention.

In particular, FIG. 1 shows a ellipsoid prolate laser ablation system 300 including a scanning ablation laser 380, a pre-operative ellipsoid fitter 320, a smoothing module 330, a post-operative spheroequivalent ellipsoid determiner 340, a prolate ablation profiler 350, and a custom prolate ablation profiler 360.

The scanning ablation laser 380 e.g., an excimer laser, 193 nm fundamental wavelength, 10 mJ/pulse max output at fundamental wavelength). An otherwise conventional scanning ablation laser 380 such as in LaserScan™ LSX excimer laser system available from LaserSight Technologies, Inc. includes an exemplary ablation laser 380.

The prolate laser ablation system 300 further includes a prolate corneal modeler controller 302, including a suitable processor (e.g., microprocessor, microcontroller, or digital signal processor (DSP)), such as the laser ablation system controller found in the LaserScan™ LSX excimer laser system.

In accordance with the principles of the present invention, the prolate corneal modeler controller 302 controls software based modules capable of determining an ellipsoidal ablation pattern and directing prolate-shaped corneal refractive surgery. While shown as separate modules in FIG. 1, spheroequivalent refractive surgery may be directed with combined modules and/or separated modules, in accordance with the principles of the present invention.

In the exemplary separation of modules shown in FIG. 1, the prolate corneal modeler controller 302 communicates with a refractive measurement input module 310. The refractive measurement input module 310 may be any suitable input device (e.g., keyboard, serial or parallel link to corneal topography equipment, etc.) which allows input of refractive measurement data.

Figure 2:
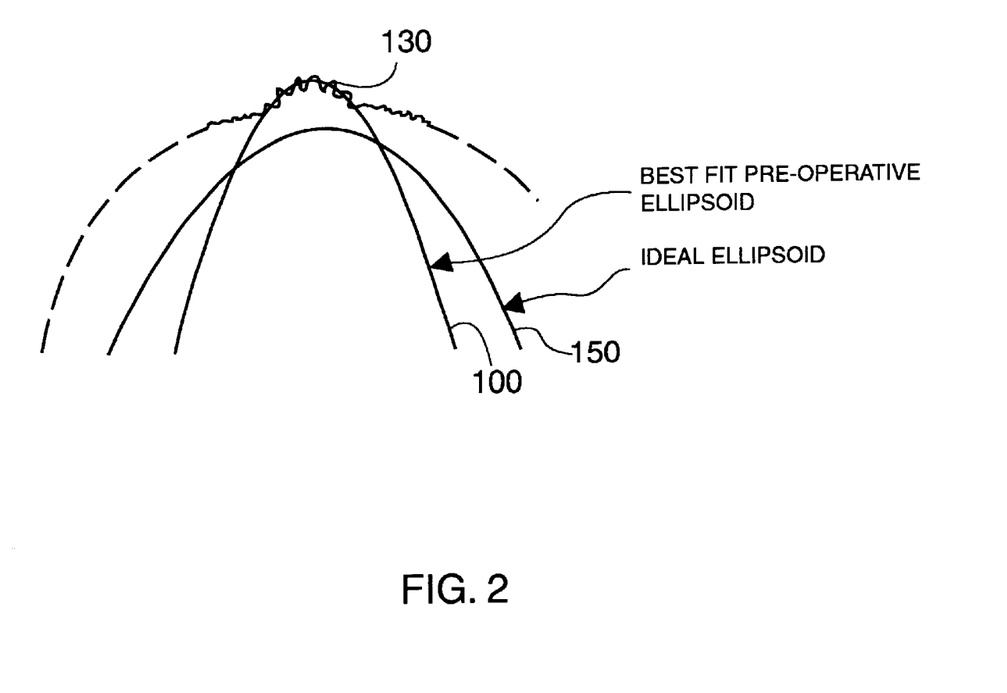
FIG. 2 depicts the use of modeling in corneal refractive surgery, in accordance with the principles of the present invention.

FIG. 2 depicts the use of modeling in corneal refractive surgery, in accordance with the principles of the present invention.

In particular, as shown in FIG. 2, a corneal surface 130 is refractively measured pre-operatively using, e.g., topographical measurements, checkered placido measurements, refractive measurements, etc. A cross-sectional view of a measured corneal surface 130 is depicted in FIG. 2.

Referring back to FIG. 1, preferably, the refractive measurement input module 310 includes a suitable measurement input program to extract three (3) or more (up to six (6) or more if necessary) preoperative exams to run on, e.g., an Eyesys 2000 system.

In the disclosed embodiment, the refractive measurement input module 310 may be adapted to also or alternatively accept three (3) or more exported exams if sent to "Custom Ablation Center" for evaluation.

The resultant refractive measurement data may result in a matrix, e.g., a 51×51 point array in patient orientation with means and standard deviations. Preferably, standard deviations are less than 1 micron. The center point (26, 26) of the 51×51 point should be the vertex zero, and all other points should relate to a mean "drop" in height from vertex in microns. Preferably, only real values are given in the 51×51 point array. If no value is given for a particular point, it is preferably left "blank", and not input as a negative number (e.g., not −1).

The pre-operative spheroequivalent ellipsoid fitter 320 utilizes the three (3) number of freedom ellipsoid modeling techniques disclosed herein to determine a best fit ellipsoid 100 to the pre-operative refractive measurements, as shown in FIG. 2.

The smoothing and/or frequency filter module 330 may utilize, e.g., a Fourier Series Bivariate using either 2 variable $2^{nd}$ order to 2 variable $5^{th}$ order. The smoothing in the disclosed embodiment was performed on the difference in each matrix point between the measured preoperative refractive measurement data and the ideal ellipsoid. This generates an "irregular difference" matrix from the best fit preoperative ellipse. The final smoothed difference matrix determines the custom ablation component, and when combined in the transfer MATRIX results in the ablation profile.

The post-operative spheroequivalent ellipsoid determiner 340 determines a desired postoperative ellipse 150 (FIG. 2) from vector analysis using the preoperative K's, preoperative refraction, desired postoperative refraction and vertex distances. All calculations are preferably calculated at the corneal plane after vertexing.

The ideal asphericity preferably maintains the Q-value. However, acceptable results are obtained when the value of $Q_{SEQ}$ for a best fit spheroequivalent ellipsoid having three (3) degrees of freedom fit to post-operative refractive measurements is between −0.25 and −0.50 postoperatively.

The prolate ablation profiler 350 determines a desired ablation profile. To compensate for oblateness due to a particular laser ablation system, the predicted oblateness from the spheroequivalent ellipsoid equation may be added to the actual pre-operative value of $Q_{SEQ}$ to give the initial Q-value for the pre-operative cornea.

For example, if the resulting cornea is more oblate from the ideal, expected spheroequivalent ellipsoidal shape by +1.00 and the patient is −0.25, a pre-operative Q-value would be +0.75, with a post-operative target of −0.25.

From these two ellipsoids, a desired ablation profile for programming into the ablation laser system may be determined for, e.g., a 6.5 mm optical zone.

A spheroequivalent ellipsoid having three (3) degrees of freedom in accordance with the principles of the present invention is capable of being used for any treatment diameter from 5 to 9 mm, where the optical zone is always 1.0 mm less than the treatment zone before blending.

The present invention may or may not be used in conjunction with custom ablation techniques. For instance, while the disclosed embodiments relate to the use of corneal topography to provide customized cornea data, the principles of the present invention relate equally to prolate ablation using only refractive measurements of the subject cornea.

In the case of custom ablation, the custom prolate ablation profiler 360 may smooth the irregular difference matrix, and/or multiplied by a correction factor transfer function based on a machine-specific calibration factor matrix 370.

The transferred smooth irregular difference matrix may then be added to the prolate ablation profile to arrive at a desired custom prolate ablation profile.

In the given example, the custom prolate ablation profile matrix may be smoothed in a particular ablation region, e.g., between the 6 and 7 mm zone, the result being a final custom prolate ablation profile matrix which is imported into the laser ablation system.

Figure 3:
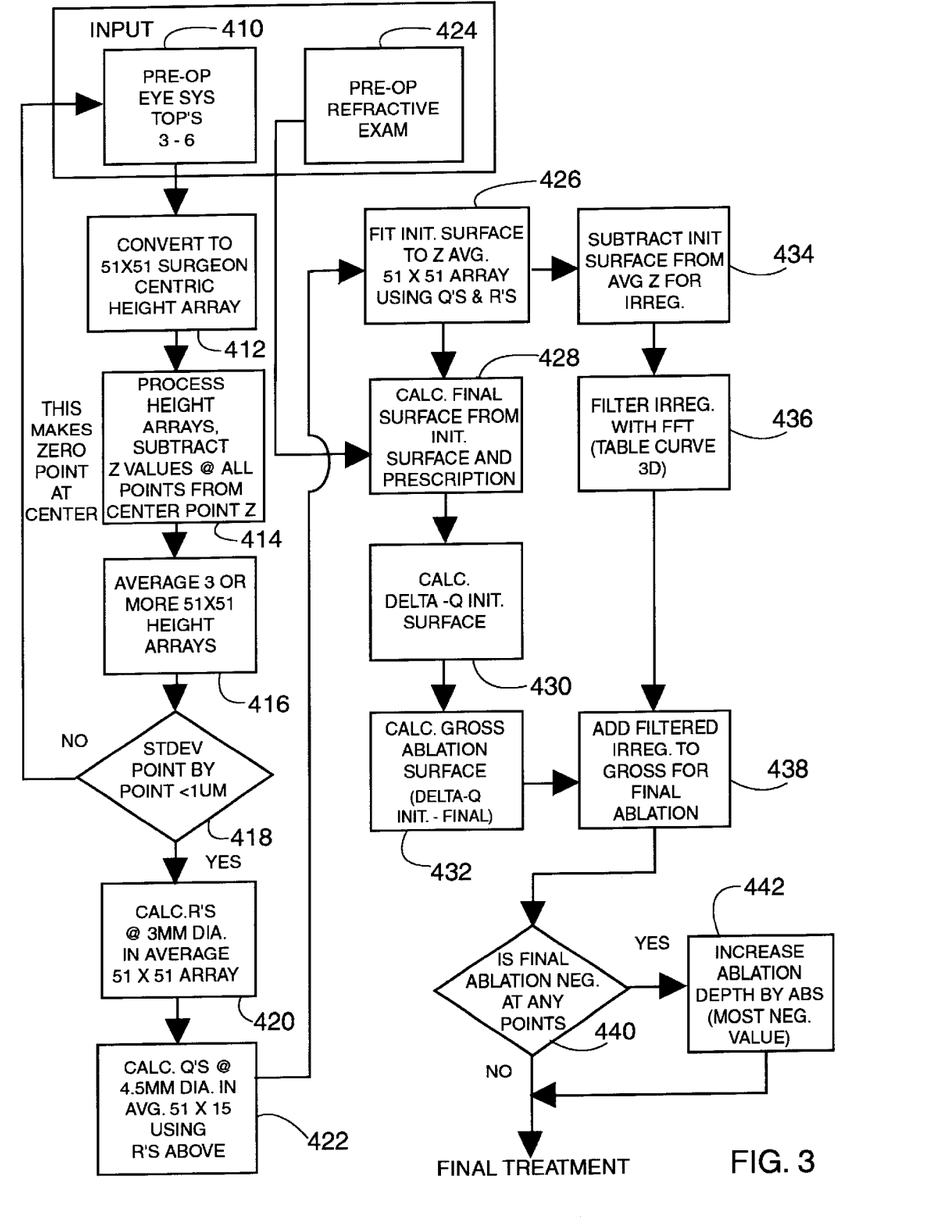
FIG. 3 shows an exemplary protocol for performing ellipsoid prolate laser ablation, in accordance with the principles of the present invention.

FIG. 3 shows an exemplary protocol for performing ellipsoid prolate laser ablation, in accordance with the principles of the present invention.

While the invention has been described with reference to the exemplary embodiments thereof, those skilled in the art will be able to make various modifications to the described embodiments of the invention without departing from the true spirit and scope of the invention.

What is claimed is:

1. A method of ablating a cornea into a prolate shape, comprising:

determining a desired ablating pattern to form a prolate shaped ellipsoid on a surface of said cornea;

adjusting an eccentricity of said prolate shaped ellipsoid to intentionally leave some astigmatism on an ablated surface of said cornea to cancel an astigmatic condition on a reverse side of said cornea; and ablating said cornea in accordance with said adjusted prolate shaped ellipsoid.

2. The method of ablating a cornea into a prolate shape according to claim 1, further comprising:

adjusting an expected depth of said desired ablation pattern in accordance with a calibration factor matrix.

3. The method of ablating a cornea into a prolate shape according to claim 2, further comprising:

empirically determining said calibration transfer matrix based on previous differences between expected ablation depths and resultant ablation depths with respect to each point on a two-dimensional matrix.

4. The method of ablating a cornea into a prolate shape according to claim 3, wherein:

said two-dimensional matrix is 51×51.

5. Apparatus for ablating a cornea into a prolate shape, comprising:

means for determining a desired ablation pattern to form a prolate shaped ellipsoid on a surface of said cornea;

means for adjusting an eccentricity of said prolate shaped ellipsoid to intentionally leave approximately 10% astigmatism on an ablated surface of said cornea to cancel an astigmatic condition on at least one of a posterior side of said cornea and a crystalline lens; and means for ablating said cornea in accordance with said adjusted prolate shaped ellipsoid.

6. The apparatus for ablating a cornea into a prolate shape according to claim 5, further comprising:

means for adjusting an expected depth of said desired ablation pattern in accordance with a calibration factor matrix.

7. The apparatus for ablating a cornea into a prolate shape according to claim 6, further comprising:

means for empirically determining said calibration factor matrix based on previous differences between expected ablation depths and resultant ablation depths with respect to each point on a two-dimensional matrix.

8. The apparatus for ablating a cornea into a prolate shape according to claim 7, wherein:

said two-dimensional matrix is 51×51.

* * * * *